United States Patent [19]
Paaren

[11] Patent Number: 5,936,105
[45] Date of Patent: Aug. 10, 1999

[54] 14-EPI-19-NOR-VITAMIN D COMPOUNDS AND METHODS

[75] Inventor: Herbert E. Paaren, Madison, Wis.

[73] Assignee: Tetrionics, Inc., Madison, Wis.

[21] Appl. No.: 09/096,330

[22] Filed: Jun. 11, 1998

Related U.S. Application Data

[60] Provisional application No. 60/053,088, Jun. 13, 1997.
[51] Int. Cl.[6] .................................................. C07C 401/00
[52] U.S. Cl. .............................................................. 552/653
[58] Field of Search ............................................... 552/653

[56] References Cited

U.S. PATENT DOCUMENTS 5,391,755  2/1995  DeLuca ..................................... 548/110
5,843,928  12/1998  Deluca et al. ........................... 514/167

*Primary Examiner*—S. Mark Clardy
*Assistant Examiner*—Alton Pryor
*Attorney, Agent, or Firm*—Ryndak & Lyerla

[57] ABSTRACT

19-nor-vitamin D analog compounds and a method of synthesizing such compounds are disclosed. More particularly, examples of such compounds include 14-epi-19-nor-1α,25-dihydroxyvitamin $D_3$, 14-epi-20-epi-19-nor-1α,25-dihydroxyvitamin $D_3$, 14-epi-20-epi-19-nor-1α-hydroxyvitamin $D_3$, 14-epi-19-nor-1α,25-dihydroxyvitamin $D_2$, 14-epi-19-nor-24-homo-1α,25-didydroxyvitamin $D_3$, 14-epi-19-nor-20(S)-hydroxymethyl-1α-hydropregnacalciferol, and 14-epi-19-nor-20(R)-hydroxymethyl-1α-hydroxypregnacalciferol.

1 Claim, No Drawings

14-EPI-19-NOR-VITAMIN D COMPOUNDS AND METHODS

This application claims the benefit of U.S. Provisional Application No. 60/053,088, filed Jun. 13, 1997.

FIELD OF THE INVENTION

The present invention relates to Vitamin D compounds and methods for making them. More specifically, the invention relates to 14-epi-19-norvitamin D analogs having good differentiative and anti-proliferative activity and little or no calcemic activity. These 14-epi-19-nor-vitamin D analogs represent a new structural class of vitamin D compounds with distinctive and advantageous biological properties.

BACKGROUND OF THE INVENTION

The natural hormone, $1\alpha,25$-dihydroxyvitamin $D_3$, is known as a highly potent regulator of calcium homeostatsis in animals and humans and its activity in cellular differentiation has also been established.

A useful therapeutic method for the treatment of malignancies is the administration of compounds that stimulate the differentiation of malignant cells to normal cells, thereby inhibiting and/or reversing the malignant transformation. For example, it has been disclosed in U.S. Pat. No. 4,391,802 that $1\alpha,25$-dihydroxyvitamin $D_3$ and $1\alpha$-hydroxyvitamin $D_3$ possess potent antileukemic activity by virtue of inducing the differentiation of malignant cells (specifically leukemia cells) to non-malignant macrophages (monocytes). These malignancies and others (e.g. breast, skin, prostate, bone, etc.) have all been shown to possess a specific intracellular protein that specifically binds $1\alpha,25$-dihydroxyvitamin $D_3$ and closely related $1\alpha$ hydroxylated vitamin D compounds. The binding of $1\alpha,25$-dihydroxyvitamin $D_3$ to the vitamin D receptor (VDR) protein initiates the sub-cellular events which bring about differentiation and anti-proliferation of malignant cells which contain the VDR protein. Consequently, these compounds are useful for the treatment of VDR positive malignancies. However, when used for such treatment, these known $1\alpha$-hydroxyvitamin D compounds have the disadvantage that they are also very potent calcemic agents which cause elevated blood calcium levels by stimulating intestinal calcium absorption and bone calcium resorption. Such activity represents the well-known classical function of these compounds. Elevated calcemic activity is, of course, a serious, undesirable side effect and unfortunately the cell differentiation activity of these compounds occurs at concentrations that elicit severe hypercalcemia.

A need exists for new vitamin D analogs that exhibit the separation of activities in cell differentiation and calcium regulation. Such a difference in activity may be useful in the treatment VDR positive cancers and other differentiative and hyperproliferative disorders. See, D. D. Bikle, *Endocrine Reviews* (1992) Vol.13, No. 4, pp. 765–784.

Chemical modification of the 1,25-dihydroxyvitamin D3 structure has yielded numerous analogs with altered biological activity. The majority of the chemical modifications have been to the C-17 side chain. To a lesser extent, structural changes have been introduced into the vitamin D ring structure. A few examples of 14-epi-Vitamin D analogs, in which the normal trans-fused C/D-ring juncture has the cis-fused configuration, have been synthesized previously. See, S. Jeganathan, A. D. Johnston, E. A. Kuenzel, A. W. Norman and W. H. Okamura, *Journal of Organic Chemistry* (1984) Vol. 49, pp. 2152–2158. However, it has been shown that these 14-epi-vitamin D analogs preferentially equilibrate to their pre-vitamin D isomer, which is opposite to the case for the normal vitamin D analogs where the equilibrium favors the vitamin structure over the corresponding pre-vitamin. The pre-vitamin D isomer has been shown to possess minimal biological activity when compared to its vitamin D counterpart, see, R. Bouillion et al. *Journal of Bone and Mineral Research* (1993) Vol. 8, No. 8, pp.1009–1015. The unstable 14-epivitamin D analogs are of little therapeutic value once isomerized to the pre-vitamin form.

The 19-nor-vitamin D structure has been synthesized previously; see, K. L. Perlman, R. E. Swenson, H. E. Paaren, H. K. Schnoes and H. F. DeLuca, *Tetrahedron Letters* (1991) pp. 7663–7666, and has been shown to possess reduced calcemic activity while retaining cellular activity similar to the natural hormone, $1\alpha,25$-dihydroxyvitamin D3.

The standardized numbering system for the natural hormone, $1\alpha,25$dihydroxyvitamin D3, and 19-nor-1,25-dihydroxyvitamin D3 where the 19-methylene group has been replaced with two hydrogens, is shown below in formula I and formula II which are as follows.

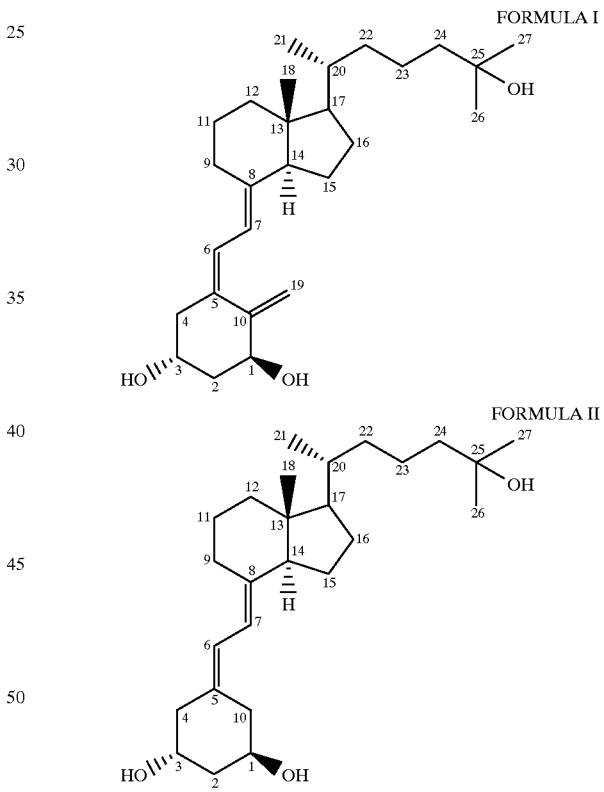

SUMMARY OF THE INVENTION

In accordance with the present invention, a new class of 19-nor-vitamin D analogs have been discovered that exhibit a desired and very advantageous activity pattern in terms of their cell differentiation activity and calcium regulation. These 14-epi-19-nor-vitamin D compounds are characterized by inversion of the C-14 center from the normal $\alpha$ configuration to the $\beta$ configuration. The 14-epi-19-nor-vitamin D structure yields a class of vitamin D compounds in which the vitamin to pre-vitamin interconversion cannot take place. Therefore, the 14-epi-19-nor-vitamin D structure is stable as the vitamin isomer, thereby retaining biological activity. As a sub-class of 14-epi-19-nor-vitamin D compounds, the 20-epi isomer is also characterized by low calcemic activity and high anti-proliferative and differentiative activity.

As a class, the 14-epi-19-nor-vitamin D analogs show lower calcemic activity than the corresponding 19-nor-vitamin D compounds and thus are more desirable therapeutic agents for the treatment of differentiative and hyperproliferative disorders.

In accordance with the present invention, 14-epi-19-nor-vitamin D analog compounds are within the general formula III as follows:

FORMULA III

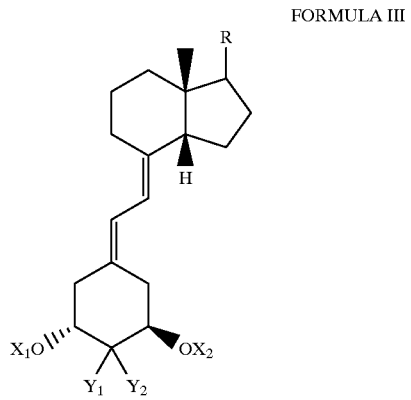

wherein the group R in the above structure represents a steroid side chain as it occurs in any of the natural vitamin D compounds, or in synthetic analogs thereof. More specifically, R may represent side chains shown below where:

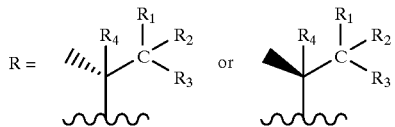

R1 is hydrogen, halogen, hydroxy, protected hydroxy, alkoxy or hydrocarbylsulphonyloxy or a group of the formula Z—$R_6$ where Z represents oxygen, sulfur, $NR_7$, SO or $CR_7R_8$, and where $R_6$, $R_7$ and $R_8$ may be the same or different, each represent a hydrogen or a straight, branched or cyclic hydrocarbon group, saturated or unsaturated, having 1–12 carbon atoms which may carry one or more substituents selected from halogen, hydroxy, protected hydroxy, alkoxy or oxo groups and $R_1$ and $R_2$ together represent an oxo group or =$CR_7R_8$ and $R_3$ or $R_4$ together or individually represent a hydrogen atom, alkyl group, hydroxy group, protected hydroxy group or alkoxy group. $X_1$ and $X_2$, which may be the same or different, represent a hydrogen, a hydroxyl protecting group or alkoxy group, $Y_1$ is hydrogen and $Y_2$ is hydrogen, alkyl, a hydroxyl, a protected hydroxyl group or alkoxy group. In addition, $Y_1$ and $Y_2$ may be the same or different and represent hydrogen, alkyl, hydroxyl, a protected hydroxyl group or an alkoxy group, or $Y_1$ and $Y_2$ together may represent a single oxo group or a single =$CR_9R_{10}$ group, where $R_9$ and $R_{10}$, together or individually, represent a hydrogen atom, alkyl group, hydroxy group or alkoxy group.

As used in the description, and in the claims, the term "hydroxy-protecting group" refers to any group commonly used for the protection of hydroxy functions during subsequent reactions, including, for example, acyl or alkylsilyl groups such as trimethylsilyl, triethylsilyl, t-butyidimethylsilyl and analogous alkyl or arylsilylradicals, or alkoxyalkyl groups such as methoxymethyl, ethoxymethyl, methoxyethoxymethyl, tetrahydrofuranyl or tetrahydropyranyl. A "protected hydroxy" is a hydroxy function derivatized by one of the hydroxy-protecting groups. "Alkyl" represents a straight-chain or branched hydrocarbon radical of 1 to 10 carbons in all its isomeric forms, such as methyl, ethyl, propyl, isopropyl, butyl, isobutyl, pentyl, etc., and the terms "hydroxyalkyl", "fluoroalkyl" and "deuteroalkyl" refer to such an alkyl radical substituted by one or more hydroxy, fluoro or deuterium groups respectively. An "acyl" group is an alkanoyl group of 1 to 6 carbons in all its isomeric forms, or an aroyl group such as benzoyl, or halo-, nitro-, or alkyl substituted benzoyl groups, or an alkoxycarbonyl group of the type Alkyl-—CO—, such as methoxycarbonyl, ethoxycarbonyl, etc., or a dicarboxylic acyl group such as oxalyl, malonyl, succinoyl, or glutaroyl. The term "aryl" signifies a phenyl-, or an alkyl-, nitro- or halo-substituted phenyl group. The term "alkoxy" signifies the group alkyl-O—.

In accordance with one aspect of the present invention, the new 14-epi-19-nor-vitamin D analog compounds have biological characteristics that include high cell differentiation and anti-proliferative activity and low calcemic activity.

Specific examples of compounds in accordance with the present invention include 14-epi-19-nor-1α,25-dihydroxyvitamin $D_3$, 14-epi-20-epi-19-nor-1α,25-dihydroxyvitamin $D_3$, 14-epi-20-epi-19-nor-1α-hydroxyvitamin $D_3$, 14-epi-19-nor-1α-hydroxyvitamin $D_3$ and 14-epi-19-nor-2methylene-1α,25-dihydroxyvitamin $D_3$. Other examples of compounds of this type are 14-epi-19-nor-1α,25-dihydroxyvitamin $D_2$, 14-epi-19-nor-24-homo-1α,25-dihydroxyvitamin $D_3$, 14-epi-19-nor-20(S)-hydroxymethyl-1α-hydroxypregnacalciferol and 14-epi-19-nor-20(R)-hydroxymethyl-1 α-hydroxypregnacalciferol. Additional examples are all of the above compounds with a hydroxy group at either the 2α or 2β position, and a 3'-hydroxypropoxy group at the 2α or 2β position.

In accordance with another aspect of the present invention, a method of synthesizing the foregoing novel compounds is provided. The synthesis method in accordance with the present invention includes the following steps: synthesis of the bicyclic ketone of Structure I where the substituent R may represent any desired group as previously defined, it being understood that any functionalities in R that might be sensitive, or that might interfere with the A-ring condensation reaction be suitably protected by methods well known in the art. Bicyclic ketones of Structure I can be prepared by known methods as documented, See, G. -D. Zhu and W. H. Okamura, Chemical Reviews (1995) Vol. 95, pp.1877–1952; epimerization of the natural C-14 stereochemistry to the 14-epi configuration by treatment with base in an alcohol solvent to yield the 14-epi-bicyclic ketone of Structure II; preparation of 19-nor-ring-A synthons of Structure III where the Z functionality represents a group the renders the hydrogen on the adjacent carbon center sufficiently acidic to yield a reactive carbanion upon treatment with strong base. Examples of such groups are —P(O)Ph$_2$, —P(O)(OAlkyl)$_2$, —SO2Ar or —Si(Alkyl)$_3$. Compounds of this type can be prepared by known methods as described in U.S. Pat. No. 5,281,731. Coupling of the A-ring synthon III with the 14-epi-bicyclic ketone II to yield the desired 14-epi-19-nor-vitamin D structure IV. The general outline of the synthetic methodology is given in the following FLOW DIAGRAM.

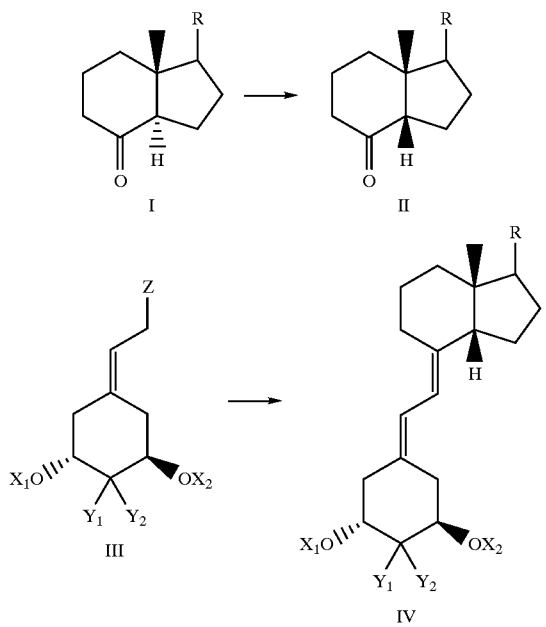

This methodology represents an application of the convergent synthesis concept which has been applied for the preparation of vitamin D compounds and 19-nor-vitamin D compounds [e.g. See, G.-D. Zhu and W. H. Okamura, *Chemical Reviews* (1995) Vol. 95, pp.1877–1952]. An alternative synthetic method would be to construct the 14-epi-19-nor-20(R) and 20(S)-hydroxymethyl vitamin compounds prior to side-chain attachment by condensation of an A-ring fragment as defined above with a suitably protected 20-hydroxymethyl-C/D-ring fragment. These derivatives could then be side-chain elaborated to the desired 14-epi-19-nor-vitamin D compounds.

The following synthetic schemes are detailed for 14-epi-19-norvitamin D analogs in which $Y_1$ and $Y_2$ are hydrogen. However, these processes are also effective in synthesizing the class of 14-epi-19-norvitamin D analogs in which $Y_1$ is hydrogen and $Y_2$ is hydrogen, alkyl, a hydroxyl, a protected hydroxyl group or alkoxy group.

Specific synthetic transformations are shown diagrammatically in Process Schemes 1, 2, 3 and 4.

SCHEME 1 shows the preparation of the De-A,B-8β-(triethylsilyloxy)-20(S)-(hydroxymethyl)-pregnane [5] and De-A,B-8β-(triethylsilyloxy)-20(R)-(hydroxymethyl)-pregnane [7] from vitamin D2. These C/D-ring isomers when coupled to the appropriate side chain fragment, oxidized and epimerized provide the necessary structure for condensation with a ring-A unit to afford the corresponding 14-epi-19-nor-vitamin D analogs.

SCHEME 2 shows the synthesis of the side chain elaborated 14-epi-8-oxo-C/D-ring synthon with the natural 20(R) stereochemistry, [13] and assembly of the 14-epi-19-nor-1α, 25-dihydroxyvitamin D3 analog [27].

SCHEME 3 shows the synthesis of the side chain elaborated 14-epi-8-oxo-C/D-ring synthons with the 20(S)-epi stereochemistry, [18] and [23]

SCHEME 4 shows the preparation of 14-epi-20-epi-19-nor-1α,25-dihydroxyvitamin $D_3$ [29] and the corresponding 14-epi-20-epi-19-nor-1 α-hydroxyvitamin $D_3$ pro-drug analog [28].

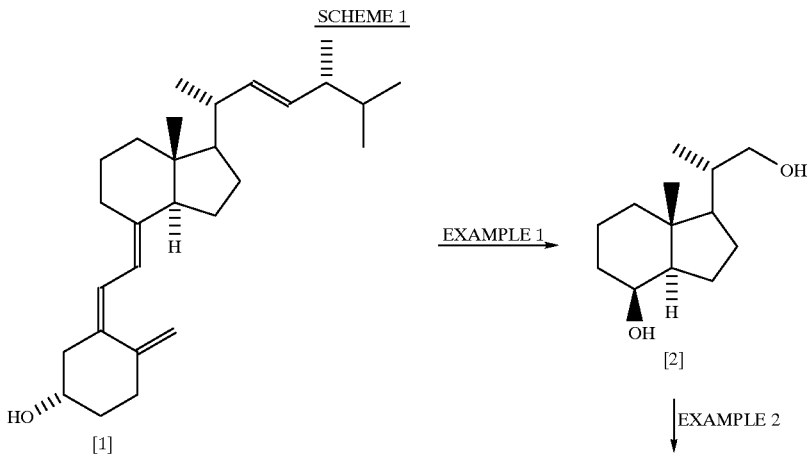

SCHEME 1

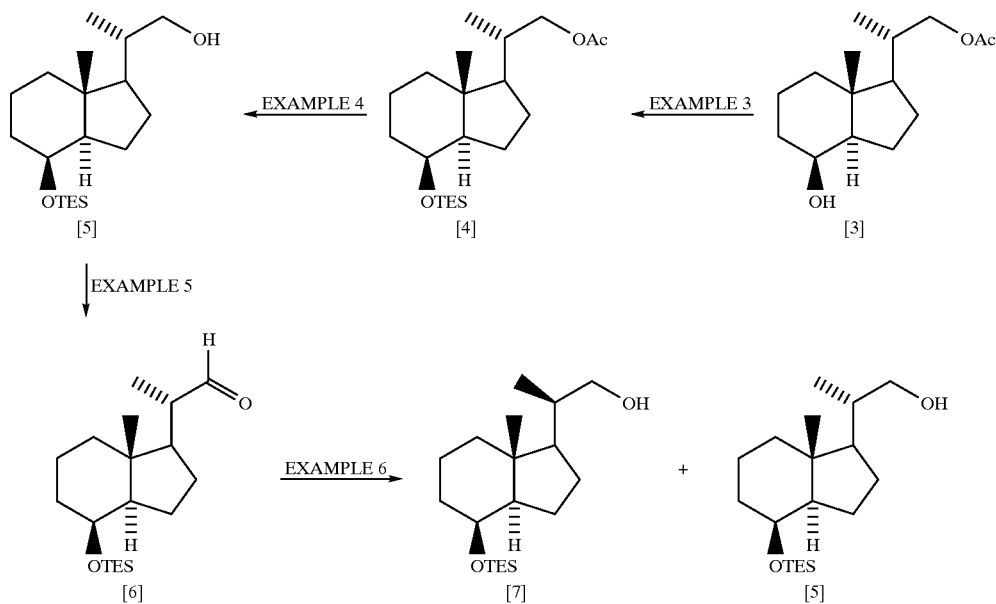
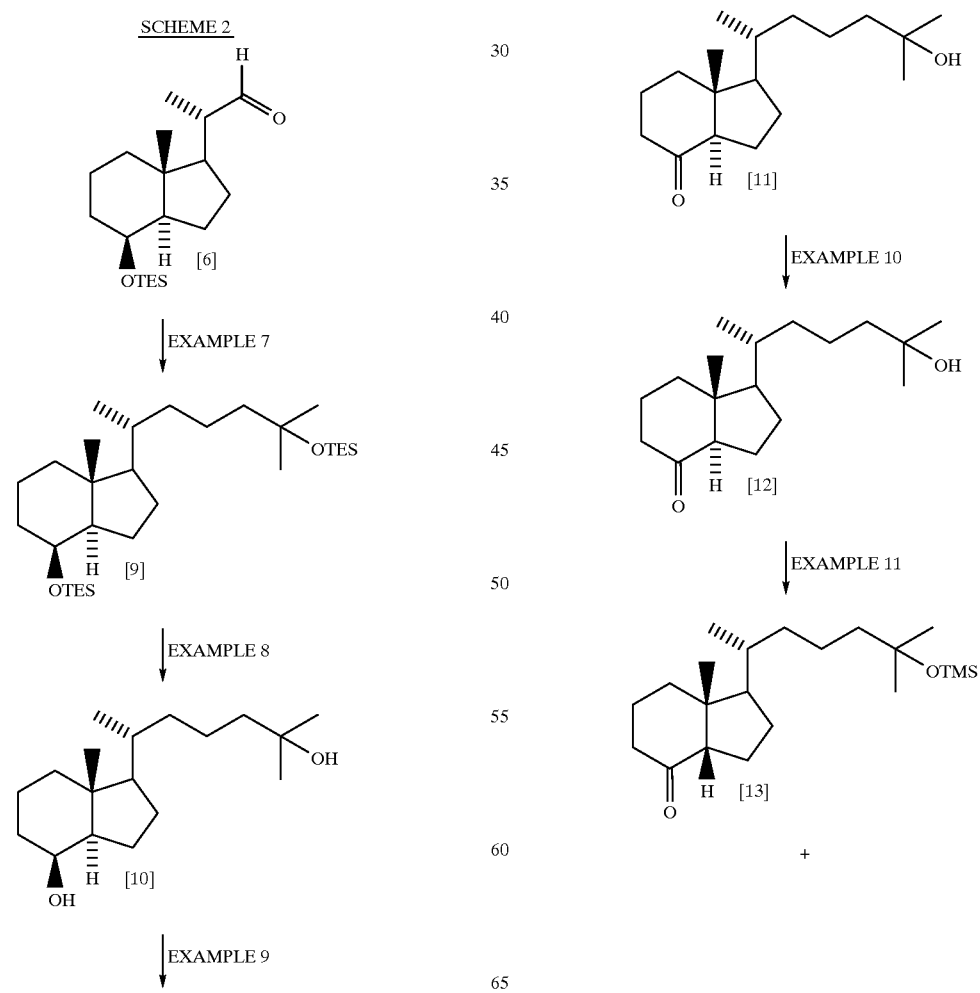

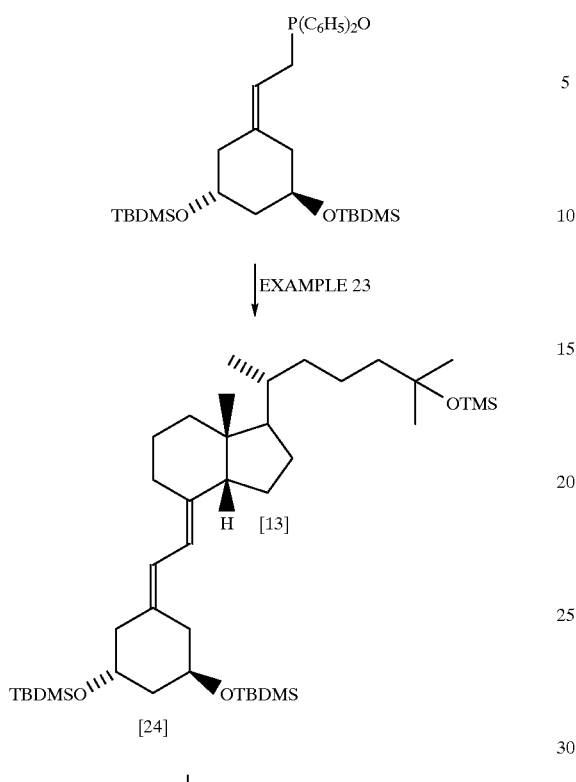
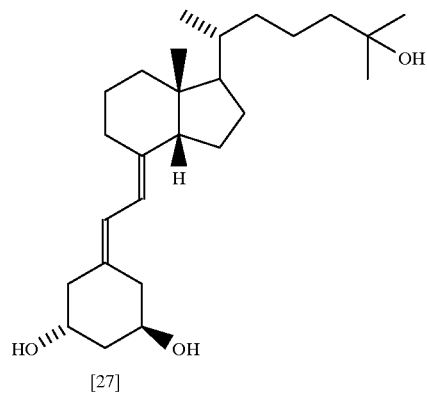
SCHEME 3
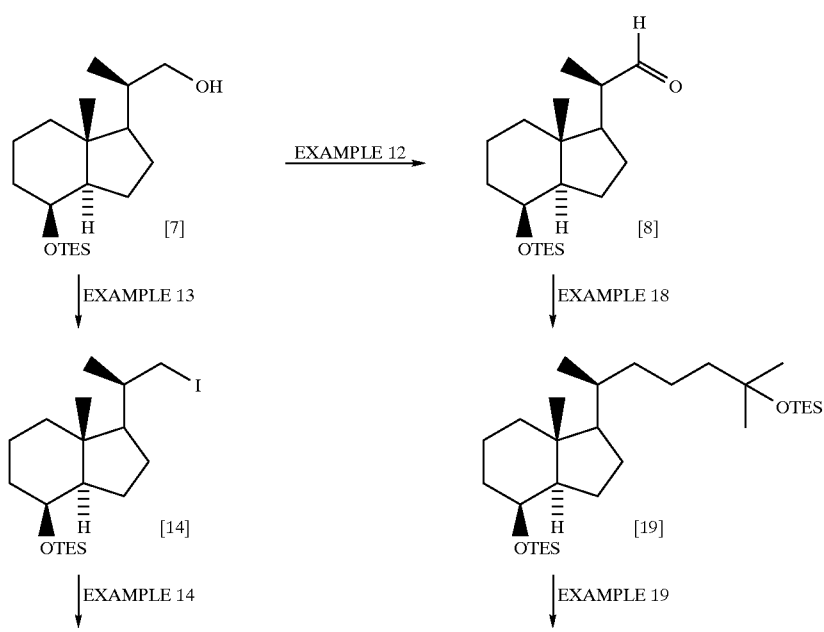

-continued
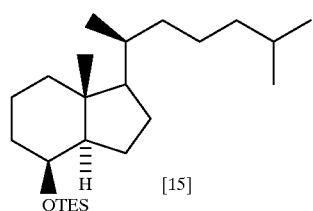 [15]
↓ EXAMPLE 15
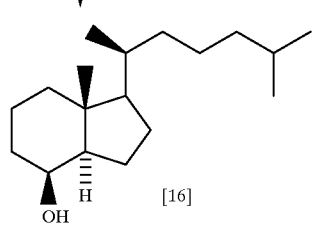 [16]
↓ EXAMPLE 16
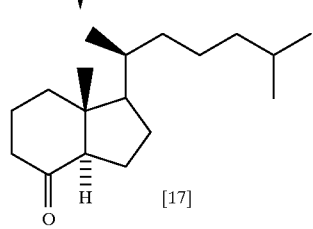 [17]
↓ EXAMPLE 17
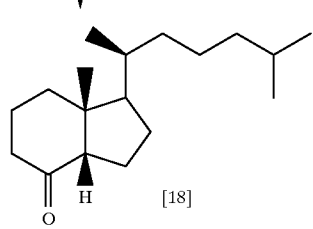 [18]
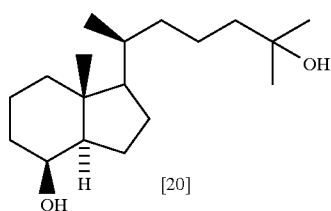 [20]
↓ EXAMPLE 20
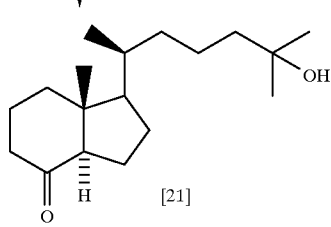 [21]
↓ EXAMPLE 21
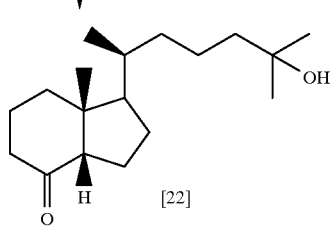 [22]
↓ EXAMPLE 22
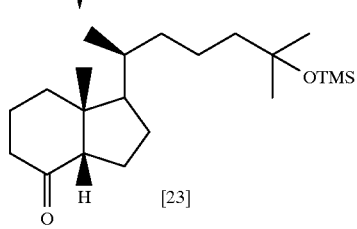 [23]
SCHEME 4
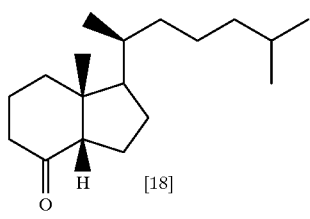 [18]
+
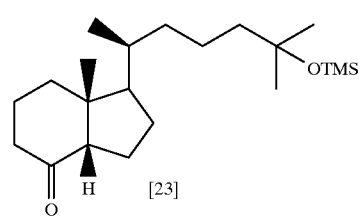 [23]
+

-continued

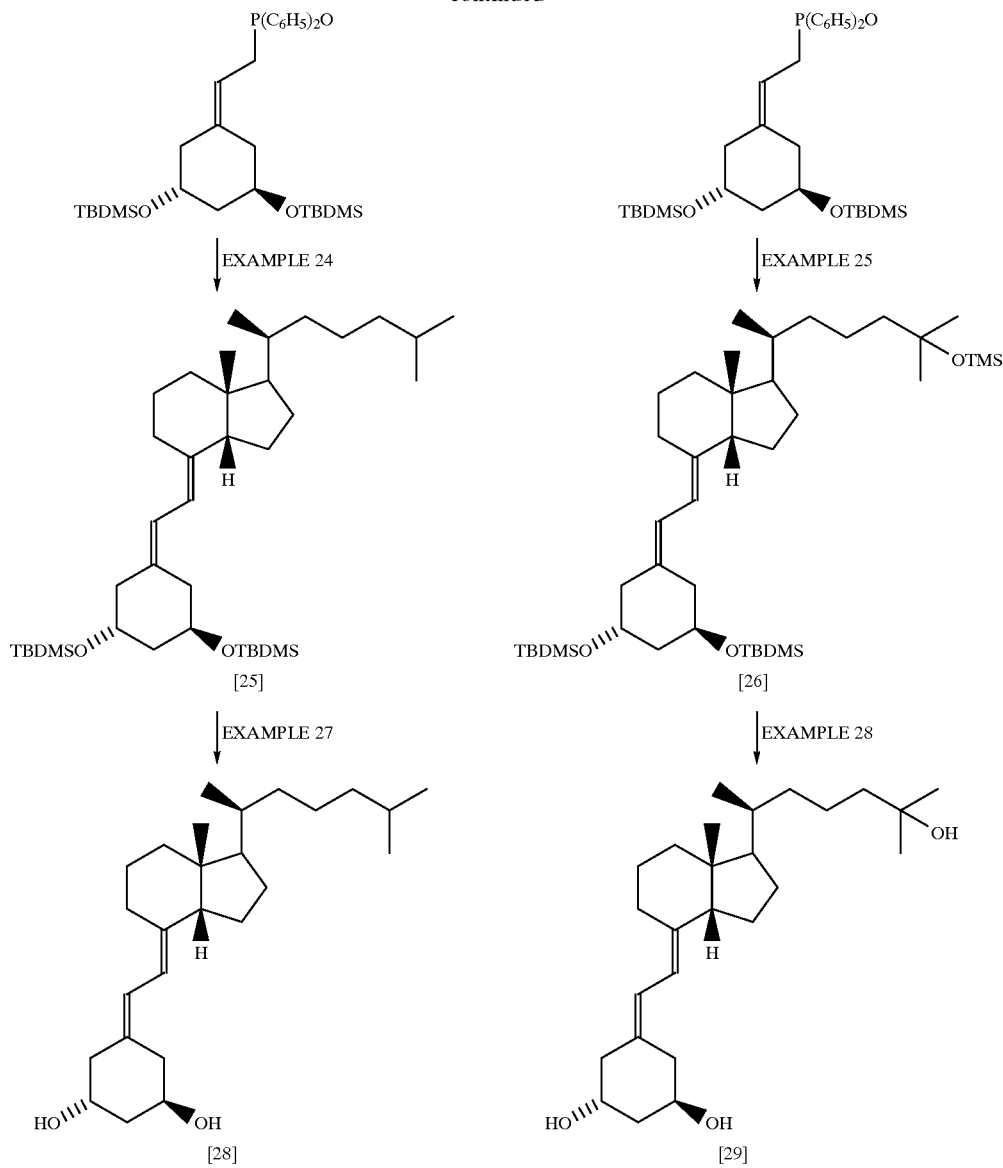

Experimental details for the chemical process steps depicted in the schemes are provided in the specific examples which follow. Compound designations by Arabic numerals (e.g., compound [1], [2], [3], etc.) as used in these examples refer to the structures so numbered in the schemes. The 19-nor-vitamin D compounds possessing the normal C-14 configuration were prepared by condensing the bicyclic ketone I, prior to base catalyzed C-14 epimerization, with the appropriate A-ring fragment. These 19-nor-vitamin D derivatives with the normal C-14 configuration were biologically evaluated along with the 14-epi-19-nor-vitamin D analogs in order to establish the beneficial effect of the 14-epi modification.

EXAMPLE 1

De-A,B-8β-hydroxy-20(S)-(hydroxymethyl)-pregnane [12]

To a stirred solution of 25.0 g of vitamin $D_2$ [1] in 1500 ml of methanol was added 15 ml of pyridine. The solution was cooled in a dry icxe/acetone bath and treated with ozone until saturation and an intense blue color was evident. The solution was purged with oxygen for 15 min. and treated with 6.0 g of sodium borohydride. The reaction was allowed to warm to room temperature treated with an additional 3.0 g of sodium borohydride followed by a final 3.0 g potion of sodium borohydride 30 min later. After an additional 30 min at room temperature, the reaction was quenched with 200 ml of water and concentrated under vacuum. The residue was extracted with 750 ml of ethyl acetate and the aqueous layer removed. The organic extract was washed with 250 ml 1N HCl, 250 ml of sat. HaHCO₃, 250 ml of sat. NaCl, dried over $Na_2SO_4$ and concentrated under vacuum to yield 17.42 g of [2] as an oil suitable for the following reaction without any further purification.

EXAMPLE 2

De-A,B-8β-hydroxy-20(S)-(acetoxymethyl)-pregnane [3]

A stirred solution of 17.42 g of [2] in 70 ml of anhy. pyridine was cooled in an ice bath and 9.0 ml of acetic anhydride was added dropwise. The reaction was maintained at ice bath temperatures for 18 hrs then quenched by addition of 100 ml of sat. NaHCO$_3$. After 30 min. the quenched reaction was extracted with 2×250 ml of ethyl acetate. The organic extracts were washed with 1N HCl until the pH of the wash was less than 1,250 ml of sat. NaHCO$_3$, 250 ml of sat. NaCl, dried over Na$_2$SO$_4$ and concentrated under vacuum to yield 17.38 g of [3] as an oil suitable for use in the next reaction without further purification.

EXAMPLE 3

De-A,B-8β-(triethylsilyloxy)-20(S) Aacetoxymethyl)-pregnane [41]

To a stirred solution of 17.38 g of [3] in 80 ml of dimethylformamide (DMF) was added 13.8 g of imidazole and mixture stirred until homogeneous. To this solution was added 11.6 ml of chloro-triethylsilane and the reaction was maintained at room temperature overnight. At the end of this time the reaction was quenched with 100 ml of ice/water and extracted with 2×250 ml of ethyl acetate. The organic extract was washed with 250 ml of 1N HCl, 250 ml of sat. NaHCO$_3$, 250 ml of sat. NaCl, dried over Na$_2$SO$_4$ and concentrated under vacuum to yield 30.0 g of crude product. This material was flashed chromatographed on 200 g of silica gel with 5% ethyl acetate in hexanes to yield 18.65 g of the desired product [4].

EXAMPLE 4

De-A,B-8β-(triethylsilyloxy)-20(S)-(hydroxymethyl)-pregnane [5]

To a stirred suspension of 2.8 g of lithium aluminum hydride (LAH) in 200 ml of anhy. ether cooled in an ice bath was added a solution of 18.65 g of [4] in 90 ml of ether dropwise over 15 min. After 20 min at ice bath temperatures the reaction was diluted with 90 ml of ether and quenched by the careful dropwise addition of 10% NaOH until a free flowing white ppt. formed. The solution was filtered and concentrated to dryness under vacuum to yield 15.8 g of the desired product [5].

EXAMPLE 5

De-A,B-8β-(triethylsilyloxy)-20(S)-formyl-pregnane [6]

To a stirred solution of 8.14 g of [5] in 125 ml of dimethyl sulfoxide (DMSO) and 62 ml of dichloromethane cooled to ice bath temperatures was added 21 ml of triethylamine followed by 19.88 g of sulfur trioxide-pyridine complex. After 30 min the reaction was concentrated under vacuum and extracted with 500 ml of ethyl acetate. The ethyl acetate extract was washed with 300 ml of water, 300 ml of sat. NaCl, dried over Na$_2$SO$_4$ and concentrated to dryness under vacuum. The crude residue was percolated through 50 g of silica gel with 20% ethyl acetate in hexanes and the eluate concentrated to dryness under vacuum to yield 7.75 g of the desired product [6].

EXAMPLE 6

De-A,B-8β-triethylsilyloxy)-20(R)-(hydroxymethyl)-preinane [7]

To a stirred solution of 5.88 g of [6] in 120 ml of methanol was added 6.10 g of NaHCO$_3$. The reaction was heated to reflux under argon for 0.5 hrs and cooled in an ice bath. To the stirred suspension was added 1.41 g of NaBH$_4$ and the ice bath was removed. After 15 min the reaction was quenched with 30 ml of water, filtered and concentrated under vacuum. The crude product was extracted with 200 ml of ethyl acetate and the organic extract was washed with 150 ml of water, 150 ml of sat. NaCl, dried over Na$_2$SO$_4$ and concentrated under vacuum to yield 5.70 g of the 20(R) and 20(S) alcohols. Flash chromatography on 245 g of silica gel in 8% ethyl acetate in hexanes yielded 2.54 g of the pure 20(R) alcohol [7] followed by 2.52 g of a mixture of the 20(R) [7] and 20(S) [5] alcohols.

EXAMPLE 7

De-A,B-8β,25-bis(triethylsilyloxy)-cholestane [19]

A flask was charged with 989 mg of freshly prepared magnesium turnings under argon. To the stirred turnings was added a solution of 5.26 g of 1-bromo-3-methyl-3-(triethylsilyloxy)-butane in 19 ml of freshly distilled THF dropwise over 25 min. After the Grignard reaction had cooled to room temperature, a solution of 3.28 g of [6] in 15 ml of THF was added dropwise over 6 min. After 15 min the reaction was quenched with water and extracted with 250 ml of ethyl acetate. The organic extract was washed with 180 ml of 1N HCl, 180 ml of sat. NaHCO$_3$, 180 ml of sat. NaCl, dried over Na$_2$SO$_4$ and concentrated to dryness under vacuum to yield 7.04 g of the crude 22-hydroxy product.

The 22-hydroxy product from the previous reaction was dissolved in 11 ml of anhy. dichloromethane and 2.71 g of thiocarbonyl-diimidazole was added. The reaction was heated to a gently reflux overnight. At the end of this time the reaction was cooled and concentrated under vacuum. The crude product was percolated through silica gel with 35% ethyl acetate in hexanes and the eluate was concentrated under vacuum to yield 7.89 g of the 22-oxythiocarbonylimidazolate.

A stirred solution of the compound from the previous reaction in 170 ml of toluene was heated to 78° C. and a solution of 4.08 ml of tributyltin hydride and 0.498 g of AIBN in 30 ml of toluene was added dropwise over 10 min. The reaction was maintained at 78° C. for an additional 30 min. then cooled to room temperature and concentrated under vacuum. The crude reaction was taken up in 300 ml of ethyl acetate and the organic solution was washed with 250 ml 1N HCl, 250 ml of sat. NaHCO$_3$, 250 ml of sat. NaCl, dried over Na$_2$SO$_4$ and concentrated under vacuum. The crude product was percolated through silica gel with hexanes and the eluate was concentrated to dryness to yield 6.66 g of the desired product [19] contaminated with alkyl tin residue.

EXAMPLE 8

De-A,B-8β,25-dihydroxycholestane [10]

To a stirred solution of 6.66 g of [9] in 80 ml of ethanol was added 4.0 g of pyridinium p-toluenesulfonate and the solution was heated to reflux for 7.5 hrs. At the end of this time the reaction was concentrated under vacuum and diluted with 125 ml of ethyl acetate. The organic solution was washed with 75 ml of sat. NaHCO$_3$, 75 ml of sat. NaCl, dried over Na$_2$SO$_4$ and concentrated to dryness under vacuum. The crude product was flash chromatographed on 60 g of silica gel with 30% ethyl acetate in hexanes to yield 1.69 g of the desired product [10].

EXAMPLE 9

De-A,B-25-hydroxy8-oxo-holestane [11]

To a stirred solution of 1.69 g of [10] in 60 ml of dichloromethane was added 4.3 g of pyridinium chlorochromate and the reaction was allowed to stir for 1.5 hr at room temp. At the end of this time the reaction was diluted with 75 ml of ether and decanted. The reaction flask was extracted with 2×40 ml portions of ether which were combined with the original reaction solution. The combined extracts were percolated through silica gel with ether and the eluate was concentrated under vacuum to yield 1.78 g of the desired product [11].

$^1$H NMR (CDCl$_3$,500 MHz,δ): 0.64 (3H,s,18-CH$_3$); 0.97 (3H,d,J=6 Hz,21-CH$_3$); 1.22 (6H,s,26&27-CH$_3$). MS, m/e (relative intensity): 280(3), M+, C$_{18}$H$_{32}$O$_2$; 262(30), M+—H$_2$O; 59(95) (CH$_3$)$_2$COH+; 55(100) H$_2$CHCO+

EXAMPLE 10

De-A,B-14-epi-25-hydroxy-8-oxo-cholestane [121]

To a stirred solution of 1.30 g of [11] in 60 ml of ethanol was added 4 ml of 10% NaOH and the reaction was allowed to stir at room temp. for 1 hr. At the end of this time the reaction was concentrated under vacuum and extracted with 150 ml of ethyl acetate. The organic extract was washed with 2×75 ml of water, 75 ml of sat. NaCl, dried over Na$_2$SO$_4$ and concentrated under vacuum to yield 1.25 g of crude product. This material was flash chromatographed on 85 g of silica gel in 20% ethyl acetate in hexanes to yield 0.79 g of the desired product [12].

$^1$H NMR (CDCl$_3$,500 MHz,δ): 1.04 (3H,s,18-CH$_3$); 0.90 (3H,d,J=6 Hz,21-CH$_3$); 1.21 (6H,s,26&27-CH$_3$). MS, m/e (relative intensity): 280(3), M+, C$_{18}$H$_{32}$O$_2$; 262(35), M+—H$_2$O; 59(80), (CH$_3$)$_2$COH+; 55(65) H$_2$CHCO+

EXAMPLE 11

De-A,B-14-epi8-oxo-25-(trimethylsilyloxy)-cholestane [13]

To a stirred solution of 107 mg of [12] in 2 ml of anhy. dichloromethane was added 220 ul of trimethylsilyl imidazole. After 45 min. the reaction was diluted with 50 ml of ethyl acetate, washed with 50 ml of sat. NaCl, dried over Na$_2$SO$_4$ and concentrated to dryness under vacuum. The crude product was percolated through silica gel with 20% ethyl acetate in hexanes to yield 129 mg of the desired product [13].

EXAMPLE 12

De-A,B-8β-(triethylsilyloxy)-20(R)-formyl-pregnane [8]

To a stirred solution of 3.20 g of [7] in 25 ml of dimethyl sulfoxide (DMSO) and 25 ml of dichloromethane cooled to ice bath temperatures was added 8.2 ml of triethylamine followed by 7.81 g of sulfur trioxide-pyridine complex. After 30 min the reaction was concentrated under vacuum and extracted with 200 ml of ethyl acetate. The ethyl acetate extract was washed with 200 ml of water, 200 ml of sat. NaCl, dried over Na$_2$SO$_4$ and concentrated to dryness under vacuum. The crude residue was percolated through 25 g of silica gel with 20% ethyl acetate in hexanes and the eluate concentrated to dryness under vacuum to yield 3.06 g of the desired product [8].

EXAMPLE 13

De-A,B-8β-(triethylsilyloxy)-20(R)-(iodomethyl)-pregnane [14]

To a stirred solution of 450 mg of [7] in 4 ml of anhy. pyridine cooled in an ice bath was added 0.79 g of p-toluenesulfonyl chloride. The reaction was placed at refrigerator temperature for 18 hrs. At the end of this time the reaction was quenched with ice and extracted with 50 ml of ethyl acetate. The organic extract was washed 2×30 ml of 1N HCl, 50 ml of sat. NaHCO$_3$, 50 ml of sat. NaCl, dried over Na$_2$SO$_4$ and concentrated to dryness under vacuum to yield 574 mg of the desired 22-tosyloxy product.

A stirred suspension of 568 mg of the 22-tosylate and 1.4 g of sodium iodide in 10 ml of acetone was heated to reflux for 5 hrs. At the end of this time the reaction was cooled to room temperature and concentrated under vacuum. The crude reaction was extracted with 50 ml of ethyl acetate and the organic extract was washed with 35 ml of water, 35 ml of sat. NaCl, dried over Na$_2$SO$_4$ and concentrated to dryness under vacuum. The crude product was percolated through silica gel with 5% ethyl acetate in hexanes and the eluate concentrated to dryness to yield 489 mg of the desired product [14].

EXAMPLE 14

De-A,B-8β-(triethylsilyloxy)-20-epi-cholestane [15]

A 25 ml oven dried flask was charged with 106 mg of freshly prepared magnesium turnings under argon. A solution of 330 mg 1-bromo-3-methylbutane in 3 ml of freshly distilled tetrahydrofuran was added dropwise over 5 min. The exothermic reaction was cooled to room temperature and transferred to a clean and dry 25 ml flask cooled in an ice bath containing 43 mg of copper(I)iodide under argon. This suspension was allowed to stir for 20 min. and a solution of the 239 mg of the 22-iodo compound [14] in 2 ml of THF was added dropwise over 5 min. After 1 hr the reaction was quenched with 2 ml of methanol and percolated through silica gel with hexanes. The eluate was concentrated to dryness under vacuum to yield 214 mg of product [15].

EXAMPLE 15

De-A,B-8β-hydroxy-20-epi-cholestane [16]

A solution of 214 mg of [15] in 4 ml of THF was treated with 4.4 ml of 1 M tetrabutylammonium fluoride in THF for 1 hr at 45° C. The reaction was cooled to room temperature and concentrated under vacuum. The crude product was extracted with 50 ml of ethyl acetate and the organic extract was washed with 2×30 ml of water, 30 ml of sat. NaCl, dried over Na$_2$SO$_4$ and concentrated to dryness to yield 175 mg of crude product. This material was flash chromatographed on 35 g of silica in 10% ethyl acetate in hexanes to yield 65 mg of the desired product [16].

EXAMPLE 16

De-A,B-20-epi-8-oxo-cholestane [17]

A stirred solution of 63 mg of [16] in 4 ml of dichloromethane was treated with 5 157 mg of pyridinium chlorochromate at room temperature. After 1 hour, the reaction was diluted with 25 ml of ether. This solution was percolated through silica gel with ether and the eluate was concentrated to dryness to yield 63 mg of the desired product [17].

$^1$H NMR (CDCl$_3$,500 MHz,δ): 0.64 (3H,s,18-CH$_3$); 0.85 (3H,d,J=6 Hz,21-CH$_3$) 0.88 (6H,d,j=7 Hz,26&27-CH$_3$). MS, m/e (relative intensity): 264(25), M+, C$_{18}$H$_{32}$O; 249 (25), M+—CH$_3$; 55(100) H$_2$CHCO+

EXAMPLE 17

De-A,B-14-epi-20-epi-8-oxo-cholestane [1]

A stirred solution of 63 mg of [17] in 3 ml of ethanol was treated with 0.2 ml of 10% NaOH at room temp. After 1 hr the reaction was concentrated under vacuum and extracted with 40 ml of ether. The organic phase was washed with 2×25 ml of water, 25 ml of sat. NaCl, dried over $Na_2SO_4$ and concentrated to dryness under vacuum. The crude product was flash chromatographed on silica gel with 5% ethyl acetate to yield 43 mg of the desired product [18].

EXAMPLE 18

De-A,B-8β,25-bis(triethylsilyloxy)-20-epi-cholestane [19]

A flask was charged with 853 mg of freshly prepared magnesium turnings under argon. To the stirred turnings was added a solution of 4.91 g of 1-bromo-3-methyl-3-(triethylsilyloxy)-butane in 15 ml of freshly distilled THF dropwise over 20 min. After the Grignard reaction had cooled to room temperature, a solution of 3.06 g of [8] in 12 ml of THF was added dropwise over 5 min. After 15 min the reaction was quenched with water and extracted with 200 ml of ethyl acetate. The organic extract was washed with 150 ml of 1N HCl, 150 ml of sat. $NaHCO_3$, 150 ml of sat. NaCl, dried over $Na_2SO_4$ and concentrated to dryness under vacuum to yield 6.64 g of the crude 22-hydroxy product.

The 22-hydroxy product from the previous reaction was dissolved in 10 ml of anhy. dichloromethane and 2.53 g of thiocarbonyl-diimidazole was added. The reaction was heated to a gently reflux overnight. At the end of this time the reaction was cooled and concentrated under vacuum. The crude product was percolated through silica gel with 35% ethyl acetate in hexanes and the eluate was concentrated under vacuum to yield 7.48 g of the 22oxythiocarbonylimidazolate.

A stirred solution of the compound from the previous reaction in 160 ml of toluene was heated to 78° C. and a solution of 3.8 ml of tributyltin hydride and 0.466 g of AIBN in 30 ml of toluene was added dropwise over 10 min. The reaction was maintained at 78° C. for an additional 30 min. then cooled to room temperature and concentrated under vacuum. The crude reaction was taken up in 300 ml of ethyl acetate and the organic solution was washed with 250 ml 1N HCl, 250 ml of sat. $NaHCO_3$, 250 ml of sat. NaCl, dried over $Na_2SO_4$ and concentrated under vacuum. The crude product was percolated through silica gel with hexanes and the eluate was concentrated to dryness to yield 7.44 g of the desired product [19] contaminated with alkyl tin residue.

EXAMPLE 19

De-A,B-8β,25-dihydroxy-20-epi-cholestane [20]

To a stirred solution of 7.44 g of [19] in 80 ml of ethanol was added 4.0 g of pyridinium p-toluenesulfonate and the solution was heated to reflux for 7.5 hrs. At the end of this time the reaction was concentrated under vacuum and diluted with 125 ml of ethyl acetate. The organic solution was washed with 75 ml of sat. $NaHCO_3$, 75 ml of sat. NaCl, dried over $Na_2SO_4$ and concentrated to dryness under vacuum. The crude product was flash chromatographed on 60 g of silica gel with 30% ethyl acetate in hexanes to yield 1.85 g of the desired product [20].

EXAMPLE 20

De-A,B-20-epi-25-hydroxy-8-oxo-cholestane [21]

To a stirred solution of 2.18 g of [20] in 80 ml of dichloromethane was added 5.47 g of pyridinium chlorochromate and the reaction was allowed to stir for 1.25 hrs at room temperature. At the end of this time the reaction was diluted with 75 ml of ether and decanted. The reaction flask was extracted with 2×40 ml portions of ether which were combined with the original reaction solution. The combined extracts were percolated through silica gel with ether and the eluate was concentrated under vacuum to yield 1.97 g of the desired product [21].

$^1$H NMR ($CDCl_3$,500 MHz,δ): 0.64 (3H,s,18-$CH_3$); 0.87 (3H,d,J=6Hz,21-$CH_3$); 1.22 (6H,s,26&27-$CH_3$). MS, m/e (relative intensity): 280(2), M+, $C_{18}H_{32}O_2$; 262(20), M+—$H_2O$; 59(90) $(CH_3)_2COH+$; 55(100) $H_2CHCO+$

EXAMPLE 21

De-A,B-14-epi-20-epi-25-hydroxy-8-oxo-cholestane [221]

To a stirred solution of 46 mg of [211 ] in 2ml of ethanol was added 150 ul of 10% NaOH. The mixture was allowed to react for 1.25 hr at room temperature then concentrated to dryness under vacuum. The crude reaction mixture was dissolved in 30 ml of ethyl acetate and washed with 30 ml of water, 30 ml of sat. NaCl, dried over $Na_2SO_4$ and concentrated to dryness under vacuum. The crude product was flash chromatographed on 27 g of silica with 25% ethyl acetate in hexanes to yield 25 mg of the desired product [22].

EXAMPLE 22

De-A,B-14epi-20-epi-8-oxo-25:(trimethylsilyloxy)-cholestane [23]

To a stirred solution of 25 mg of [22] in 2 ml of anhy. dichloromethane was added 150 ul of trimethylsilylimidazole under argon and the reaction was maintained at room temperature for 9 hrs. At the end of this time the reaction was quenched with a small amount of ice then diluted with 30 ml of ethyl acetate. The organic solution was washed with 20 ml of water, 20 ml of sat. NaCl, dried over $Na_2SO_4$ and concentrated to dryness under vacuum. The crude product was flash chromatographed on 20 g of silica gel with 10% ethyl acetate in hexanes to yield 25 mg of the desired product [23].

EXAMPLE 23

14-epi-19-nor-1α,3β-bis(t-butyldimethylsilyloxy)-25-(trimethylsilyloxy)-vitamin $D_3$ [24]

To a stirred solution of 0.84 g of the 19-nor-A-ring phosphine oxide ▢ in 3 ml of freshly distilled THF cooled to dry ice/acetone temperature under argon was added 0.865 ml of 1.7M n-butyl lithium in hexanes dropwise over 5 min. After 25 min. a solution of0.129 g of [13] in 2.5 ml of THF was added dropwise over 10 min. The reaction was maintained at dry ice/acetone temperature for 3 hrs then allowed to warm to room temperature. At the end of this time the reaction was quenched with 2 ml of water diluted with 50 ml of ethyl acetate, washed with 25 ml of sat. $NaHCO_3$, 25 ml of sat. NaCl, dried over $Na_2SO_4$ and concentrated under vacuum. The crude product was flash chromatographed on 20 g of silica gel in 2% ethyl acetate in hexanes to yield 235 mg of the desired compound [24].

EXAMPLE 24

14-epi-20-epi-19-nor-1α,3β-bis(t-butyldimethylsilyloxy)-vitamin $D_3$ [25]

To a stirred solution of 367 mg of the A-ring phosphine oxide ▢ in 2 ml of freshly distilled THF cooled to −30° C.

under argon was added 360 ul of 1.7M n-butyl lithium in hexanes dropwise over 1 min. The reaction was allowed to stir at −30° C. for 30 min then cooled in a dry ice/acetone bath to −78° C. To this deep red solution was added 42.5 mg of [18] in 2 ml of THF dropwise over 10 min. The reaction was maintained at −78° C. for 3 hrs the slowly warmed to room temperature. The reaction was quenched with 2 ml of water and diluted with 50 ml of ethyl acetate. The ethyl acetate solution was washed with 30 ml of sat. NaCl, dried over $Na_2SO_4$ and concentrated to dryness under vacuum to yield 397 mg of crude product. This material was percolated through silica gel with 3% ethyl acetate in hexanes and the eluate concentrated under vacuum to yield 105 mg of the desired product [25].

EXAMPLE 25
14-epi-20-epi-19-nor-1α,3β-bis(t-butyldimethylsilyloxy)-25-(trimethylsilyloxy)-vitamin $D_3$, [26]

To a stirred solution of 160 mg of the A-ring phosphine oxide ☐ in 2 ml of freshly distilled THF cooled to −30° C.

$^1$H NMR (CDCl$_3$, 500 MHz, δ): 0.93 (3H, s, 18-CH$_3$); 0.89 (3H, d, J = 7 Hz, 21-CH$_3$); 1.23 (6H, s, 26 & 27-CH$_3$); 4.08 (1H, m, 1-CH); 4.08 (1H, m, 3-CH); 6.04 (1H, d, J = 14 Hz, 7-CH); 6.26 (1H, d, J = 14 Hz, 6-CH).

under argon was added 150 ul of 1.7M n-butyl lithium in hexanes dropwise over 1 min. The reaction was allowed to stir at −30° C. for 30 min then cooled in a dry ice/acetone bath to −78° C. To this deep red solution was added 25 mg of [23] in 2 ml of THF dropwise over 10 min. The reaction was maintained at −78° C. for 3 hrs then slowly warmed to room temperature. The reaction was quenched with 1 ml of water and diluted with 30 ml of ethyl acetate. The ethyl acetate solution was washed with 20 ml of sat. NaCl, dried over $Na_2SO_4$ and concentrated to dryness under vacuum to yield 200 mg of crude product. This material was percolated through silica gel with 5% ethyl acetate in hexanes and the eluate concentrated under vacuum to yield 44 mg of the desired product [26].

EXAMPLE 26

14epi-19-nor-1α,25-dihydroxyvitamin $D_3$ [27]

To a stirred solution of 235 mg of [24] in 2 ml of THF was added 2 ml of 1M tetrabutylammonium fluoride in THF and the reaction was brought to 70° C. for 1.5 hr. At the end of this time the reaction was cooled, concentrated under vacuum and diluted with 50 ml of ethyl acetate. The organic solution was washed with 30 ml of water, 30 ml of sat. NaCl, dried over $Na_2SO_4$ and concentrated under vacuum. The crude product was flash chromatographed on 20 g of silica gel in 35% acetone in hexanes to yield 123 mg of the desired product [27].

MS, m/e (relative intensity): 404(10), M+, $C_{26}H_{44}O_3$; 386(32), M+—$H_2O$; 275(10), M+—side chain; 59(100) ($CH_3)_2$COH+; UV (ε): 252 nm (33,000)

EXAMPLE 27
14-epi-20-epi-19-nor-1α-hydroxyvitamin $D_3$ [28]

To a stirred solution of 99 mg of [25] in 3 ml of THF was added 1.3 ml of 1M tetrabutylammonium fluoride in THF and the reaction was brought to 45° C. for 3 hrs. At the end of this time the reaction was cooled and concentrated under vacuum. The crude reaction was extracted with 50 ml of ethyl acetate and the organic extract was washed with 3×30 ml of water, 30 ml of sat. NaCl, dried over $Na_2SO_4$ and concentrated under vacuum to yield 93 mg of crude product. This material was flash chromatographed on 35 g of silica gel with 35% ethyl acetate in hexanes to yield 52 mg of the desired product [28].

$^1$H NMR (CDCl$_3$, 500 MHz, δ): 0.93 (3H, s, 18-CH$_3$); 0.82 (3H, d, J = 7 Hz, 21-CH$_3$); 0.87 (6H, d, J = 7 Hz, 26 & 27-CH$_3$); 4.10 (1H, m, 1-CH); 4.10 (1H, m, 3-CH); 6.04 (1H, d, J = 14 Hz, 7-CH); 6.26 (1H, d, J = 14 Hz, 6-CH).

MS, m/e (relative intensity): 388(80), M+, $C_{26}H_{44}O_2$; 275(20), M+—side chain; UV (ε): 252 nm (41,000)

EXAMPLE 28

14-epi-20-epi-19-nor-1α,25-dihydroxyvitamin $D_3$ [29]

A stirred solution of 44 mg of [26] in 1.5 ml tetrahydrofuran (THF) was heated to 45° C. and 1.5 ml of a 1 M solution of tetrabutylammonium fluoride in THF was added. After 2.5 hrs at 45° C. the reaction was concentrated under vacuum and extracted with 50 ml of ethyl acetate. The organic extract was washed with 3×30 ml of water, 30 ml of sat. NaCl, dried over $Na_2SO_4$ and concentrated under vacuum to yield 38.8 mg of the crude 19-nor vitamin analog. The crude product was flash chromatographed on 35 g of silica gel with 40% acetone in hexanes to yield 21.2 mg of the desired product [29].

$^1$H NMR (CDCl$_3$, 500 MHz, δ): 0.93 (3H, s, 18-CH$_3$); 0.85 (3H, d, J = 7 Hz, 21-CH$_3$); 1.21 (6H, s, 26 & 27-CH$_3$); 4.10 (1H, m, 1-CH); 4.10 (1H, m, 3-CH); 6.04 (1H, d, J = 14 Hz, 7-CH); 6.26 (1H, d, J = 14 Hz, 6-CH).

MS, m/e (relative intensity): 404(25), M+, C$_{26}$H$_{44}$O$_3$; 386(70), M+—H$_2$O; 275(20), M+—side chain; 59(100) (CH$_3$)$_2$COH+; UV (ε): 252 nm (38.000)

BIOLOGICAL ACTIVITY

The 14-epi-19-nor-vitamin D analogs were compared to the corresponding 19-nor-vitamin D compounds for; 1) ability to bind the Vitamin D Receptor (VDR) protein, 2) ability to induce differentiation and antiproliferative activity in a HL-60 cell line, and 3) calcemic activity in vitamin D deficient rat, using established assays known in the art. The assay procedures and results obtained are described in more detail in the following Examples.

EXAMPLE 29

Binding to the Procine Intestinal Nuclear Vitamin D Receptor.

The ability of the 14-epi-19-nor vitamin D analogs and the corresponding 19-nor-vitamin D analogs to displace radiolabeled 1α,25-dihdyroxyvitamin D$_3$ from the vitamin D receptor (VDR) protein was measured and the concentration required to effect 50% (EC$_{50}$) displacement of label is given below.

|  | EC$_{50}$ | Activity vs. 1,25(OH)$_2$D$_3$ |
|---|---|---|
| 1,25(OH)$_2$D$_3$ | 0.82 nM | 1.0 |
| 19-nor-1,25(OH)$_2$D$_3$ | 4.20 nM | 0.2 |
| 14-epi-19-nor-1,25(OH)$_2$D$_3$[27] | 4.50 nM | 0.18 |
| 20-epi-19-nor-1,25(OH)$_2$D$_3$ | 0.80 nM | 1.0 |
| 14-epi-20-epi-19-nor-1,25(OH)$_2$D$_3$8 29] | 2.50 nM | 0.33 |
| 20-epi-19-nor-1(OH)D$_3$ | 600 nM | 0.0013 |
| 14-epi-20-epi-19-nor-1(OH)D$_3$[28] | >1000 nM | <0.0008 |

EXAMPLE 30

Differentiation of HL-60 Cells.

The ability of the 14-epi-19-nor-vitamin analogs and the corresponding 19-nor-vitamin D analogs to induce differentiation in the human HL-60 promyelocyte cell line was measured by a nitroblue tetrazolium (NBT) reduction assay. The results are given as the concentration necessary to induce differentiation in 50% of the cells (IC$_{50}$).

|  | EC$_{50}$ | Activity vs. 1,25(OH)$_2$D$_3$ |
|---|---|---|
| 1,25(OH)$_2$D$_3$ | 0.5 nM | 1.0 |
| 19-nor-1,25(OH)$_2$D$_3$ | 13 nM | 0.40 |
| 14-epi-19-nor-1,25(OH)$_2$D$_3$[27] | 15 nM | 0.33 |
| 20-epi-19-nor-1,25(OH)$_2$D$_3$ | 0.2 nM | 25 |
| 14-epi-20-epi-19-nor-1,25(OH)$_2$D$_3$[29]. | 0.5 nM | 10.0 |

EXAMPLE 31

Inhibition of HL-60 Cell Proliferation.

The ability of the 14-epi-19-nor-vitamin D analogs and the corresponding 19-nor-vitamin D analogs to inhibit proliferation of the HL-60 cell line was measured by thymidine incorporation assay. The results are given as the concentration necessary to bring about a 50% reduction in thymidine incorporation (IC$_{50}$).

|  | EC$_{50}$ | Activity vs. 1,25(OH)$_2$D$_3$ |
|---|---|---|
| 1,25(OH)$_2$D$_3$ | 30 nM | 1.0 |
| 19-nor-1,25(OH)$_2$D$_3$ | 60 nM | 0.5 |
| 14-epi-19-nor-1,25(OH)$_2$D$_3$[27] | 80 nM | 0.4 |
| 20-epi-19-nor-1,25(OH)$_2$D$_3$ | 4.0 nM | 7.5 |
| 14-epi-20-epi-19-nor-1,25(OH)$_2$D$_3$[29]. | 0.66 nM | 45 |

EXAMPLE 32

In vivo Calcemic Activity

The biological activity of the 14-epi-19-nor-vitamin D analogs and the corresponding 19-nor-vitamin D analogs was evaluated in terms of their ability to induce intestinal calcium transport and bone calcium mobilization in the D deficient rat. These studies were carried out with five to six rats per group. Male weanling rats were fed a vitamin D-deficient diet for one week and then shifted to the same diet but with calcium removed for three weeks. The hypocalcemic rats were dosed intraperitoneally with the indicated dose of compound per day for a total of 7 days. Twenty-four hours after the last dose all animals were killed by decapitation and serum calcium was measured by atomic absorption spectroscopy in the presence of 1.0% lanthanium chloride. Intestinal calcium transport was measureed by the everted gut sac technique of of Martin and Deluca.

TABLE 1

19-nor-1-hydroxyvitamin D analogs

| GROUP | AMOUNT (pmol/d/7 days) | TRANSPORT (S/M) | SERUM CALCIUM (mg/100 ml) |
|---|---|---|---|
| D-Deficient | 0 | 3.4 ± 0.5 | 3.1 ± 0.1 |
| 1(OH)D$_3$ | 250 | 8.1 ± 0.1 | 4.8 ± 0.3 |
|  | 625 | 10.6 ± 1.4 | 5.9 ± 0.1 |
| 19-nor-1(OH)D$_3$ | 250 | 6.3 ± 0.7 | 3.4 ± 0.2 |
|  | 625 | 8.6 ± 0.7 | 3.7 ± 0.2 |
|  | 1390 | 7.2 ± 0.2 | 3.8 ± 0.2 |
| 20-epi-19-nor-1(OH)D$_3$ | 250 | 7.6 ± 0.5 | 4.1 ± 0.1 |
|  | 625 | 9.2 ± 1.1 | 5.4 ± 0.3 |
|  | 1300 | 11.7 ± 1.4 | 6.7 ± 0.2 |

The results are the average of 5 rats (mean ± SEM)

TABLE 2

19-nor-1,25-dihydroxyvitamin D analogs

| GROUP | AMOUNT (pmol/d/7 days) | TRANSPORT (S/M) | SERUM CALCIUM (mg/100 ml) |
|---|---|---|---|
| D-Deficient | 0 | 3.1 ± 0.1 | 3.4 ± 0.1 |
| 1,25(OH)$_2$D$_3$ | 250 | 7.8 ± 0.4 | 5.3 ± 0.3 |
| 19-nor-1,25(OH)$_2$D$_3$ | 250 | 4.8 ± 0.4 | 3.6 ± 0.1 |
|  | 625 | 4.9 ± 0.5 | 3.6 ± 0.2 |

TABLE 2-continued 19-nor-1,25-dihydroxyvitamin D analogs

| GROUP | AMOUNT (pmol/d/7 days) | TRANSPORT (S/M) | SERUM CALCIUM (mg/100 ml) |
|---|---|---|---|
|  | 1300 | 4.8 ± 0.5 | 3.7 ± 0.2 |
| 20-epi-19-nor- | 250 | 7.3 ± 0.1 | 5.7 ± 0.5 |
| 1,25(OH)$_2$D$_3$ | 625 | 8.2 ± 0.7 | 6.3 ± 0.4 |
|  | 1300 | 8.7 ± 0.7 | 6.6 ± 0.5 |
| 14-epi-19-nor- | 250 | 4.1 ± 0.4 | 3.6 ± 0.2 |
| 1,25(OH)$_2$D$_3$[27] | 625 | 3.2 ± 0.4 | 3.2 ± 0.1 |
|  | 1300 | 3.5 ± 0.3 | 3.4 ± 0.1 |

The results are the average of 5 rats (mean ± SEM)

TABLE 3

14-epi-20-epi-19-nor-vitamin D analogs

| GROUP | AMOUNT (pmol/d/7 days) | TRANSPORT (S/M) | SERUM CALCIUM (mg/100 ml) |
|---|---|---|---|
| D-Deficient | 0 | 3.46 ± 0.27 | 3.92 ± 0.11 |
| 1,25(OH)$_2$D$_3$ | 260 | 7.18 ± 0.47 | 5.36 ± 0.27 |
| 14-epi-20-epi-19- | 260 | 3.80 ± 0.23 | 3.96 ± 0.05 |
| nor-1(OH)D$_3$ | 625 | 5.14 ± 0.66 | 4.11 ± 0.10 |
| [28] | 1300 | 5.90 ± 0.49 | 3.79 ± 0.05 |
| 14-epi-20-epi-19- | 260 | 4.36 ± 0.30 | 4.02 ± 0.16 |
| nor-1,25(OH)$_2$D$_3$ | 625 | 6.94 ± 0.27 | 3.66 ± 0.06 |
| [29] | 1300 | 7.14 ± 0.44 | 4.10 ± 0.20 |

The results are the average of 6 rats (mean ± SEM)

ANALYSIS OF RESULTS

The in vitro activity of the 14-epi-19-nor-1α,25-dihydroxyvitamin D analogs shows these compounds possess excellent differentiative (D) and anti-proliferative (I) properties. The most potent analog is the 20-epi isomer [29]. The 14-epi-20-epi-19-nor-1,25-(OH)$_2$D$_3$ compound [29] is 10(D) to 45(I) times more potent than 1,25-(OH)$_2$D$_3$. The 19-nor-14-epi analog [27] is approximately half as active as 1,25-(OH)$_2$D$_3$.

The in vitro efficacy data must be interpreted in conjunction with the analogs in vivo calcemic activity which estimates toxicity. The 14-epi-19-nor analog [27] shows no calcemic activity at 5x the dose of 1,25-(OH)$_2$D$_3$ and therefore has a calcemic activity less than 20% of the natural hormone. The actual calcemic activity of this analog may be significantly lower because the dose response curve was not extended to a point where an equivalent response relative to 1,25-(OH)$_2$D$_3$ was obtained. The calcemic activity of this analog may be extremely low. The calcemic response of the 14-epi-20-epi isomer [29] is also greatly reduced. It is important to note that the 14-epi-20epi isomer [29] shows only minimal gut activity (20% of the natural hormone) and no effect on bone at any of the doses tested. These results indicate an extremely favorable spectrum of activity for analog [29].

The overall anti-cancer efficacy of these analogs may be represented as a ratio defined by differentiative activity (D) and anti-proliferative activity (I) relative to calcemic activity. If the ratios of (D) activity and (I) activity to calcemic activity for 1,25-(OH)$_2$D$_3$ are taken to be 1, ratios with ranges greater than 1 indicate therapeutic potential greater than the natural hormone.

Therapeutic Potential (T.P.)=cellular activity/calcemic activity
14-epi-19-nor-1α,25-(OH)$_2$D$_3$ [27]
T.P.=0.33(D)/<<0.2–0.4(I)/<<0.2=>>1.7(D)–2.0(I)
14-epi-20-epi-19-nor-1α25-(OH)$_2$D$_3$ [29]
T.P.=8.0(D)/<0.2–56(I)/<0.2=>40(D)–280(I)

The therapeutic potential for each of the 14-epi-19-nor-drug analogs is more favorable than 1,25-(OH)$_2$D$_3$. The 14-epi-20-epi-19-nor analog [29], possess the highest ratio. The analog with the normal C-20 configuration [27] has a lower therapeutic potential, however, this value can be expected to increase once the full dose response curve for calcemic activity has been established.

The in vivo results also establish the PRO-DRUG concept for the 14-epi-19-nor-25-deoxy-analog [28]. The pro-drug 14-epi-20-epi-19-nor-1α-hydroxyvitamin D$_3$ [28] elicits biological activity In vivo similar to the 25hydroxylated analog [29], confirming that it has been 25-hydroxylated by the liver. The 14-epi-20-epi-19-nor analog [28] also shows reduced activity on gut compared to the 25-hydroxy drug compound and no activity on bone. This minimal bone activity resulting in lower calcemic toxicity may have important clinical implications.

IMPORTANCE OF FINDINGS

The 14-epi-19-nor-vitamin D drug analogs, [27] and [29], show an enhanced therapeutic potential relative to the natural hormone, 1α,25-(OH)$_2$D$_3$, for the treatment of VDR positive malignancies. The introduction of the 14-epi modification into the 20-epi-19-nor structure results in a compound with greatly reduced calcemic activity and accentuated cellular activity. The 14-epi-20-epi-19-nor-1,25-(OH)$_2$D$_3$ analog [29] has a therapeutic potential exceeding the natural hormone by two orders of magnitude. The 14-epi-19-nor analog with the natural 20(R) configuration [27] possesses cellular activity similar to the native hormone while having greatly reduced calcemic activity.

The corresponding 19-nor pro-drug congener, [28], has been shown to be activated in vivo to the active drug product. These results also indicate that rapid metabolic clearance is not a factor in the low calcemic activity of the 19-nor-vitamin D analogs. These preliminary results suggest that the pro-drugs may be less toxic due to diminished activity on bone.

Hence, the 14-epi-19-nor vitamin D analogs that were synthesized and evaluated in the present invention represent an effective practical embodiment of the concept of differentiative therapy of hyperproliferative disorders and diseases.

Another aspect of the above invention are pharmaceutical preparations of the 14-epi-19-nor-vitamin D compounds which can be formulated as solutions in innocuous solvents, or as emulsions, suspensions or dispersions in suitable innocuous solvents or carriers, or as pills, tablets or capsules by conventional methods known in the art, given that such formulations may also contain other pharmaceutically acceptable and non-toxic excipients, such as stabilizers, anti-oxidants, binders, coloring agents or emulsifying or taste modifying agents and that such formulations can be advantageously administered by injection, or by intravenous infusion of suitable sterile solutions, or in the form of oral doses via the alimentary canal, or by topical application.

I claim:

1. A pharmaceutical composition comprising an active ingredient, said active ingredient being the vitamin D compound 14-epi-19-nor-2-methylene-1α,25-dihydroxyvitamin D$_3$, together with a pharmaceutically acceptable excipient.

* * * * *